United States Patent [19]

Hornung et al.

[11] Patent Number: 5,529,718
[45] Date of Patent: Jun. 25, 1996

[54] SMECTIC LIQUID-CRYSTAL MIXTURE

[75] Inventors: Barbara Hornung, Hasselroth; Dietmar Jungbauer, Weiterstadt; Javier Manero, Frankfurt am Main, all of Germany

[73] Assignee: Hoechst Aktiengesellschaft, Germany

[21] Appl. No.: 278,059

[22] Filed: Jul. 20, 1994

[30] Foreign Application Priority Data

Jul. 22, 1993 [DE] Germany ................. 43 24 630.3

[51] Int. Cl.$^6$ .................... C09K 19/34; C09K 19/52; G02F 1/13
[52] U.S. Cl. .................. 252/299.61; 252/299.01; 252/299.62; 252/299.63; 252/299.67; 359/103
[58] Field of Search .................. 252/299.01, 299.61, 252/299.62, 299.63, 299.67; 359/103

[56] References Cited

U.S. PATENT DOCUMENTS

| | | | |
|---|---|---|---|
| 5,292,453 | 3/1994 | Shinjo et al. | 252/299.61 |
| 5,391,318 | 2/1995 | Yamashita et al. | 252/299.61 |

FOREIGN PATENT DOCUMENTS

| | | |
|---|---|---|
| 0206228 | 12/1986 | European Pat. Off. . |
| 0225195 | 6/1987 | European Pat. Off. . |
| 0356672 | 3/1990 | European Pat. Off. . |
| 0541081 | 5/1993 | European Pat. Off. . |
| WO86/06401 | 11/1986 | WIPO . |

OTHER PUBLICATIONS

Demus and Zaschke, Flussige Kristalle in Tabellen.

L. A. Beresnev et al., 1984, "On Mechanisms of Dipolar Ordering in Ferroelectric Liquid Crystals."

*Primary Examiner*—Shean C. Wu
*Attorney, Agent, or Firm*—Curtis, Morris & Safford

[57] ABSTRACT

A smectic liquid-crystal mixture containing rod-shaped molecules having only one side chain and certain phenylpyrimidine derivatives. The liquid-crystal mixtures according to the invention are distinguished by a low melting point and a high $S_C/S_A$ phase-transition temperature. The use of bisesters of the formula I allows the number of phenylpyrimidine derivatives in the mixtures according to the invention to be significantly reduced. Ferroelectric mixtures according to the invention have, in particular, high contrast, good alignment, a large margin, low flicker and a large angle in the chevron geometry.

20 Claims, No Drawings

SMECTIC LIQUID-CRYSTAL MIXTURE

BACKGROUND OF INVENTION

1. Field of Invention

The invention relates to a smectic, liquid-crystal mixture based on rod-shaped molecules having only one side chain and certain phenylpyrimidine derivatives.

2. Description of the Related Art

Due to their unusual combination of anisotropic and fluid behavior, liquid crystals (LCs) have found a multiplicity of possible applications in electro-optical switching and display devices.

In addition to the nematic liquid-crystal phases which have been employed for some time, smectic liquid-crystal phases, in particular ferroelectric liquid crystal phases (FLCs), have increasingly also been used recently.

Switching and display devices which contain ferroelectric liquid-crystal mixtures ("FLC light valves") have been disclosed, for example, in EP-B 0 032 362 (=U.S. Pat. No. 4,367,924). LC light valves are devices which, for example due to electrical switching, change their optical transmission characteristics in such a way that incident (and possibly re-reflected) light is modulated in intensity. Examples are the knownwatch and calculator displays or LC displays in the area of office communication and television. However, these also include light shutters, as employed, for example, in photocopiers and printers. Spatial light modulators are also areas of application of LC light valves (see Liquid Crystal Device Handbook, Nikkan Kogyo Shimbun, Tokyo, 1989; ISBN 4-526-02590-9C 3054, and the papers cited therein).

The, electro-optical switching and display devices mentioned are generally constructed in such a way that the FLC layer is surrounded on both sides by layers which are usually, in this sequence starting from the FLC layer, at least one alignment layer, electrodes and a limiting plate (for example made of glass). In addition, they contain at least one polarizer if they are operated in "guest-host" mode or in reflective mode, or two polarizers if the transmissive birefringence mode is used. The switching and display elements may, if desired, contain further auxiliary layers, such as diffusion barrier layers or insulation layers.

The abovementioned alignment layers are usually rubbed films of organic polymers or obliquely vapor-deposited silicon oxide and vary from one display manufacturer to the next.

At a sufficiently small separation of the limiting plates, the alignment layers bring the FLC molecules into a configuration in which the molecules lie with their long axes parallel to one another and the smectic planes are arranged perpendicular or inclined to the alignment layer. In this arrangement, the molecules have two equivalent alignments, between which they can be switched by applying an electric field in a pulsed manner.

In order to achieve a uniform planar alignment in the $S_C$ phase over the entire display, it is advantageous for the phase sequence of the liquid-crystal mixture to be as follows, with decreasing temperature: isotropic-nematic -smectic A-smectic C (see, for example, K. Flatischler et al., Mol. Cryst. Liq. Cryst. 131, 21 (1985); T. Matsumoto et al., pp. 468–470, Proc. of the 6th Int. Display Research Conf., Japan Display, 30 Sep.–2 Oct. 1986, Tokyo, Japan; M. Murakami et al., ibid., pp. 344–347).

In addition, for ferroelectric (chiral, smectic) liquid-crystal mixtures, the condition must be satisfied that the pitch of the helix is sufficiently large in the $S_C$ phase to prevent the formation of a helix in the display and is so large in the $N^*$ phase that the cooling process in the display is not accompanied by formation of a twisted state, but instead by formation of a homogeneous, nematic phase. The formation of a uniform, planar alignment in the display is necessary, inter alia, to achieve high contrast.

The to- and- fro switching of the molecules (and thus bright or dark setting for a fixed polarizer setting) takes place, as mentioned above, due to pulsed application of an electric field. Owing to the histability of the FLC molecules, voltage must only be present for an alignment change. A subdivision of the display into individual pixels is achieved by the known matrix arrangement of the electrodes. The electrodes are generally on the insides of the outer plates of the display, with the rows on one outer plate and the columns on the other. In the crossover areas, the pixels B, the liquid crystal between lines and columns is switched. A basic description of multiplex addressing for FLC displays is given, for example, in Proc. SID 28/2, 211 (1978), and Ferroelectrics 94, 3 (1989).

The response time $\tau$ of the FLC mixture in the display is inversely proportional to the spontaneous polarization $P_s$ and is in the region of microseconds.

$$\tau \sim \frac{\eta \cdot \sin^2 \theta}{P_s \cdot E}$$

E=strength of the applied electric field
$\eta$=rotational viscosity
$\theta$=tilt angle or half the switching angle In addition to the spontaneous polarization, the tilt angle $\theta$, i.e. the angle between the n-director, i.e. the average molecule direction, and the layer normals, is of considerable importance. Together with the birefringence $\Delta n$ and the layer thickness d, it affects the brightness of the display in accordance with the relationship:

$$T = T_o \sin^2(4\theta) \cdot \sin^2\left(\frac{\pi \cdot \Delta n \cdot d}{\lambda}\right)$$

where $T_o$ is the intensity and $\lambda$ the wavelength of the incident light.

In the case of a matrix arrangement of the electrodes in the display, the columns are usually the electrodes to which information-carrying pulses (also known as column or data pulses) are applied. The lines are then activated sequentially in a stroboscope-like manner by electric pulses, which is the prerequisite for information transfer to the pixels of the lines. An important property of the display is the time necessary for building up or changing an image. For many applications, it should be as short as possible.

Since the lines are addressed sequentially, a crucial factor is the time for which a line has to be addressed to enter information. This writing time is shorter, the shorter the voltage pulses necessary for switching the liquid crystal. In general, the maximum voltage which has to be applied is prescribed by the choice of driver, so that the pulse width necessary for switching should be kept as small as possible.

To good approximation, the product of the requisite pulse width and voltage (=pulse height) is constant, i.e. independent of the voltage, so that the pulse area just necessary for switching (CPA=critical pulse area) represents a parameter which characterizes the speed of the liquid crystal well. The CPA should be as small as possible.

The, rotational viscosity can thus also be determined as follows (see above formula for $\tau$):

$$\eta = \frac{P_s \cdot CPA}{\sin^2 \theta}$$

It is furthermore advantageous for the LC mixture in the display to have a high margin and low flicker (J. Dijon et al., Ferroelectrics 113 (1991) 371).

Margin is taken to mean the voltage range, for a given addressing scheme, in which the pulse height must be so that the LC phase switches fully. The margin is affected by the bias, i.e. the ratio of line and data pulse voltage. The margin should be as large as possible in order to compensate for thickness and temperature variations in the display.

In the case of multiplex addressing, the molecules of the unselected lines experience a deflection from their rest state due to the data pulses and then relax again. The variation in brightness caused by this is known as flicker. The flicker results in a reduction in contrast. Rieker et al. [Phys. Rev. Lett. 59, 2658 (1987)] have shown that, on cooling from the isotropic phase through the $S_A$ phase, the $S_C$ phase in displays forms a so-called chevron geometry, i.e. the layers are bent. For this reason, the effective tilt angle $\theta_{eff}$ must be employed in the above relationship between the tilt angle and transmission. The effective tilt angle is the angle between the projections of smectic normals and the optical axis of the liquid crystal onto the glass surface of the cell.

A display can either be operated in the chevron geometry which forms naturally during the cooling operation or in the so-called quasi-bookshelf geometry (QBG), into which the liquid crystal can be brought by specific field treatment (see, for example, H. Rieger et al., SID 91 Digest (Anaheim) 1991, p. 396).

It is almost impossible to achieve good values for the majority of the abovementioned parameters using individual substances. For this reason, mixtures of various substances have been used for some time (see, for example, L. A. Beresnev, L. M. Blinov, Zh. Vsws. Khim. 0-VA28 (1983) 149). Such mixtures generally comprise an achiral base mixture and optically active dopes.

The schiral base mixture should ensure a broad $S_C$ phase in a favorable temperature range. Furthermore, the achiral base mixture should have the phase sequence I-N-$S_A$-$S_C$ and the lowest possible melting point. The optically active dopes then generally serve to induce ferroelectricity in the mixture, for pitch compensation and for matching of the optical and dielectric anisotropies.

In spite of the successes achieved by the mixtures hitherto in the provision of novel LC materials, the development of FLC mixtures, or components for such mixtures, can in no way be regarded as complete. The manufacturers of display elements ("displays") continue to be interested in a broad range of different mixtures, and thus also individual components, for diverse areas of application.

It is known that certain derivatives of phenylpyrimidine, in particular 5-alkyl-2-(4-alkoxyphenyl)pyrimidines, can form $S_C$, $S_A$ and N phases (D. Demus and H. Zaschke, "Fl üssigkristalle in Tabellen" [Liquid Crystals in Tables], VEB Deutscher Verlag far Grundstoffindustrie, Leipzig 1974, pp. 260–261) and in addition can be converted into FLC mixtures by addition of optically active dopes (see, for example, M. L. Blinov et al., Ferroelectrics 59 (1984) 1–201 EP-A 0 206 228 and EP-A 0 225 195).

It is furthermore known that it is advantageous to employ at least three different phenylpyrimidine derivatives in ferroelectric liquid-crystal mixtures (WO 86/06401). EP-A 0 356 672 describes bisesters of 2-(4-hydroxy-phenyl)- 5-hydroxypyrimidine in combination with certain optically active phenylpyrimidines as components of FLC mixtures.

SUMMARY OF THE INVENTION

Surprisingly, it has now been found that bisesters of 2-(4-hydroxyphenyl)-5-hydroxypyrimidine together with mesogenic compounds carrying only one side chain form achiral base mixtures and, on addition of optically active dopes, also form ferroelectric liquid-crystal mixtures having an excellent property profile.

Mesogenic compounds having only one side chain are disclosed in EP-A 0 541 081.

DESCRIPTION OF THE PREFERRED EMBODIMENTS

The invention therefore relates to a liquid-crystal mixture comprising a) at least one bisester of the formula I

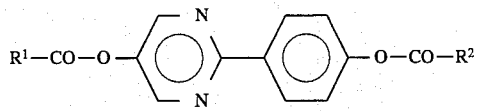

in which $R^1$ and $R^2$ are identical or different and are unbranched or branched alkyl chains having 1 or 3 to 20 carbon atoms, in which, in addition, one or more H atoms may be replaced by fluorine, and b) at least one compound having only one side chain of the formula II

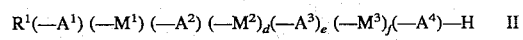

in which $R^1$ is a straight-chain or branched alkyl radical having 1 to 22 or 3 to 22 carbon atoms respectively, where one or two non-adjacent —$CH_2$— groups may also be replaced by —O—, —CO—; —CO—O—, —O—CO—, —O—CO—O— or —Si ($CH_3$)$_2$—;

$A^1$, $A^2$, $A^3$ and $A^4$ are identical or different and are 1,4-phenylene, in which one or two H atoms may be replaced by F or CN, pyridine-2,5-diyl, in which one or two H atoms may be replaced by F, pyrimidine-2,5-diyl, in which one or two H atoms may be replaced by F, trans-1,4-cyclohexylene, 1,3,4-thiadiazole-2,5-diyl or naphthalene- 2,6-diyl;

$M^1$, $M^2$ and $M^3$ are identical or different and are —CO—O—, —O—CO—, —$CH_2$—O—, —O—$CH_2$— or —$CH_2$—$CH_2$—, and a, b, c, d, e and f are zero or one, with the proviso that the sum a+c+e is 0, 1, 2 or 3.

Some of the compounds of the formula I are known and some are new.

The invention therefore also relates to 4-(5-heptanoyloxypyrimidin- 2-yl) phenyl nonanoate.

The invention furthermore relates to the use of 4-(5-heptanoyloxylpyrimidin- 2-yl)phenyl nonanoate in liquid-crystal mixtures, in particular ferroelectric liquid-crystal mixtures.

The mixtures according to the invention are distinguished by a low melting point and a high $S_C/S_A$ phase-transition temperature. Use of bisesters of the formula I gives smectic liquid-crystal mixtures having an excellent property profile which contain only a small number of phenylpyrimidine derivatives as per WO 86/06041.

Ferroelectric mixtures according to the invention are distinguished, in particular, by high contrast, good alignment, a large margin, low flicker and a large angle in the chevron geometry.

Preferred compounds of the formula I are those in which $R^1$ and $R^2$, independently of one another, are a straight-chain alkyl group having 6 to 12 carbon atoms.

Particular preference is given to the compounds 4-(5-heptanoyloxypyrimidin-2-yl)phenyl heptanoate,
4-(5-octanoyloxypyrimidin-2-yl)phenyl heptanoate,
4-(5-nonanoyloxypyrimidin-2-yl)phenyl heptanoate,
4-(5-decanoyloxypyrimidin-2-yl)phenyl heptanoate,
4-(5-undecanoyloxypyrimidin-2-yl)phenyl heptanoate,
4-(5-dodecanoyloxypyrimidin-2-yl)phenyl heptanoate,
4-(5-tridecanoyloxypyrimidin-2-yl)phenyl heptanoate,
4-(5-heptanoyloxypyrimidin-2-yl)phenyl octanoate,
4-(5-octanoyloxypyrimidin-2-yl)phenyl octanoate,
4-(5-nonanoyloxypyrimidin-2-yl)phenyl octanoate,
4-(5-decanoyloxypyrimidin-2-yl)phenyl octanoate,
4-(5-undecanoyloxypyrimidin-2-yl)phenyl octanoate,
4-(5-dodecanoyloxypyrimidin-2-yl)phenyl octanoate,
4-(5-tridecanoyloxypyrimidin-2-yl)phenyl octanoate,
4-(5-heptanoyloxypyrimidin-2-yl)phenyl nonanoate,
4-(5-octanoyloxypyrimidin-2-yl)phenyl nonanoate,
4-(5-nonanoyloxypyrimidin-2-yl)phenyl nonanoate,
4-(5-decanoyloxypyrimtdin-2-yl)phenyl nonanoate,
4-(5-undecanoyloxypyrimidin-2-yl)phenyl nonanoate,
4-(5-dodecanoyloxypyrimidin-2-yl)phenyl nonanoate,
4-(5-tridecanoyloxypyrimidin-2-yl)phenyl nonanoate,
4-(5-heptanoyloxypyrimidin-2-yl)phenyl decanoate,
4-(5-octanoyloxypyrimidin-2-yl)phenyl decanoate,
4-(5-nonanoyloxypyrimidin-2-yl)phenyl decanoate,
4-(5-decanoyloxypyrimidin-2-yl)phenyl decanoate,
4-(5-undecanoyloxypyrimidin-2-yl)phenyl decanoate,
4-(5-dodecanoyloxypyrimidin-2-yl)phenyl decanoate,
4-(5-tridecanoyloxypyrimidin-2-yl)phenyl decanoate,
4-(5-heptanoyloxypyrimidin-2-yl)phenyl undecanoate,
4-(5-octanoyloxypyrimidin-2-yl)phenyl undecanoate,
4-(5-nonanoyloxypyrimidin-2-yl)phenyl undecanoate,
4-(5-decanoyloxypyrimidin-2-yl)phenyl undecanoate,
4-(5-undecanoyloxypyrimidin-2-yl)phenyl undecanoate,
4-(5-dodecanoyloxypyrimidin-2-yl)phenyl undecanoate,
4-(5-tridecanoyloxypyrimidin-2-yl)phenyl undecanoate,
4-(5-heptanoyloxypyrimidin-2-yl)phenyl dodecanoate,
4-(5-octanoyloxypyrimidin-2-yl)phenyl dodecanoate,
4-(5-nonanoyloxypyrimidin-2-yl)phenyl dodecanoate,
4-(5-decanoyloxypyrimidin-2-yl) phenyl dodecanoate,
4-(5-undecanoyloxypyrimidin-2-yl)phenyl dodecanoate,
4-(5-dodecanoyloxypyrimidin-2-yl)phenyl dodecanoate,
4-(5-tridecanoyloxypyrimidin-2-yl)phenyl dodecanoate,
4-(5-heptanoyloxypyrimidin-2-yl)phenyl tridecanoate,
4-(5-octanoyloxypyrimidin-2-yl)phenyl tridecanoate,
4-(5-nonanoyloxypyrimidin-2-yl)phenyl tridecanoate,
4-(5-decanoyloxypyrimidin-2-yl)phenyl tridecanoate,
4-(5-undecanoyloxypyrimidin-2-yl)phenyl tridecanoate,
4-(5-dodecanoyloxypyrimidin-2-yl)phenyl tridecanoate,
4-(5-tridecanoyloxypyrimidin-2-yl)phenyl tridecanoate.

The compounds of the formula (I) can be prepared, for exhale, by reacting suitable phenols with carboxylic acids in the presence of water-binding agents or with condensation reagents such as N,N'-carbonyldiimidazole, dicyclohexylcarbodiimide or ethyl azodicarboxylate/triphenylphosphine. They can also be synthesized, inter alia, by reacting acid halides in the presence of acid scavengers, in particular pyridine, triethylamine, N-methylmorpholine or basic ion exchangers. These reactions and the conditions under which they proceed are known per se from the literature (see, for example, Houben-Weyl, Methoden der organischen Chemie, Georg Thieme Verlag, Stuttgart). An illustrative synthesis of a compound, 4-(5-heptanoyloxypyrimidin-2-yl)phenyl nonanoate, is described below.

Synthesis of 4-(5-heptanoyloxypyrimidin-2-yl) phenyl nonanoate:

a) 1.60 g of nonanoic acid are dissolved in 50 ml of absolute dichloromethane, and 2.7 g of 4-(5-benzyloxypyrimidin- 2-yl) phenol are added. 2.1 g of dicyclohexylcarbodiimide and 0.05 g of dimethylaminopyridine are added, and the mixture is stirred at room temperature for 18 hours. The mixture is filtered, and the solvent is stripped off in vacuo. The residue is chromatographed on silica gel. The product, 4-(5-benzyloxypyrimidin-2-yl)phenyl nonanoate, is recrystallized from n-hexane.

Yield: 3.5 g b) 3.5 g of 4-(5-benzyloxypyrimidin-2-yl)phenyl nonanoate are dissolved in 100 ml of THF, 0.5 g of 10% Pd on activated charcoal is added, and the mixture is hydrogenated at 25° C. with stirring. The mixture is filtered through corolite, and the solvent is removed in vacuo, giving 2.5 g of 4-(5-hydroxyprimidin-2-yl)phenyl nonanoate.

The synthesis of compounds of the formula II is described in EP-A 0 541 081 and the references cited therein.

Preferred compounds having only one side chain of the formula II are those in which the symbols and indices have the following meanings:

$R^1$ is a straight-chain alkyl radical having 1 to 14 carbon atoms, where one or two non-adjacent —$CH_2$— groups may also be replaced by —O—CO—, —CO—O—, —O—CO—, —O—CO—O— or —Si$(CH_3)_2$—;

$A^1$, $A^2$, $A^3$ and $A^4$ are identical or different and are 1,4-phenylene, in which one or two H atoms may also be replaced by F, pyrimidine-2,5-diyl, in which one or two H atoms may also be replaced by F, trans-1,4-cyclohexylene, 1,3,4-thiadiazole-2,5-diyl or pyridine-2,5-diyl, in which one or two H atoms may also be replaced by F.

Particular preference is given to compounds of the formulae IIa to IIq

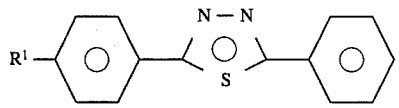

IIa

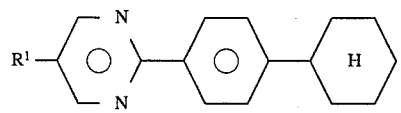

IIb

-continued

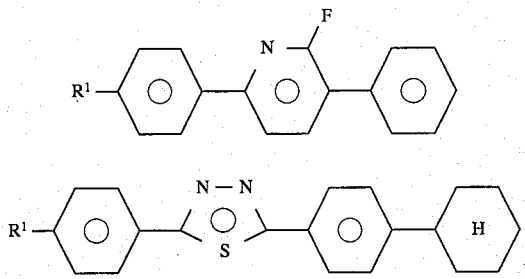
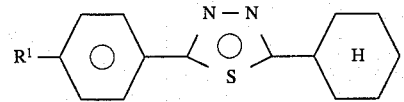
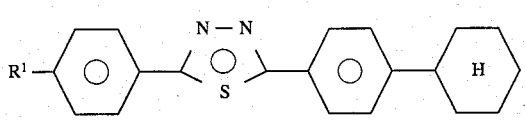
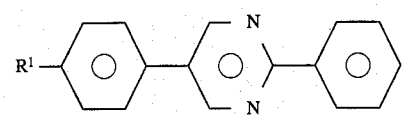
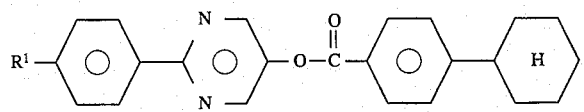
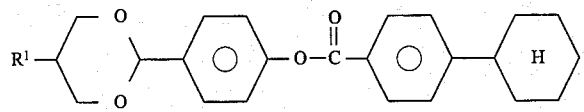
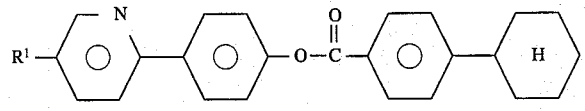
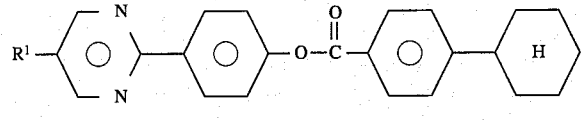
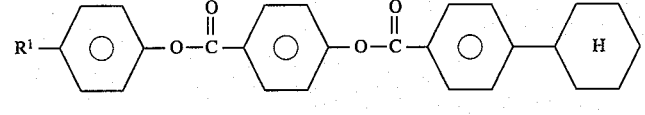
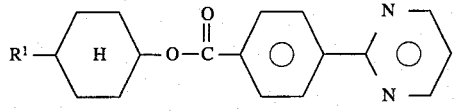
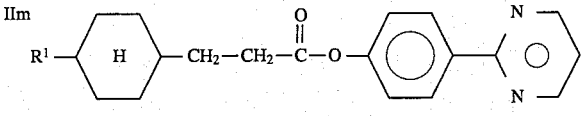
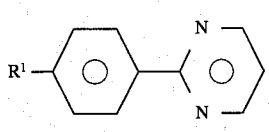
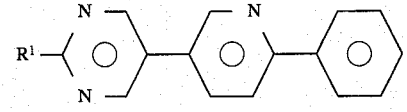
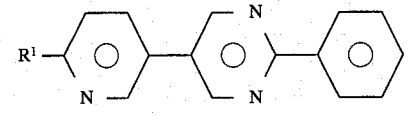

In addition to components a and b, the mixtures according to the invention can also contain further components. Ferroelectric mixtures according to the invention contain at least one further chiral, non-racemic compound.

Mixtures according to the invention contain from 0.01 to 80% by weight, preferably from 1 to 60% by weight, of each of compounds of the formulae I and II. Mixtures according to the invention preferably contain 1 to 5, particularly preferably 1 to 3, in particular 1 or 2, compounds of the formula I and 1 to 5, particularly preferably 1 to 3, compounds of the formula II. The mixtures according to the invention preferably contain a total of 2 to 35, particularly preferably 2 to 20, individual components.

In order to prepare the mixtures according to the invention, the individual substances are, for example, stirred in the isotropic phase and freed from particles and suspended matter via suitable filters.

Further components of mixtures according to the invention are preferably selected from known compounds having smectic and/or nematic and/or cholesteric phases. These include, for example:

derivatives of phenylpyrimidine, as described, for example, in WO 86/06401 and U.S. Pat. No. 4,874,542, meta-substituted aromatic compounds having a six-membered ring, as described, for example, in EP-A 0 578 054, silicon compounds, as described, for example, in EP-A 0 355 008, hydroquinone derivatives, as described, for example, in German Patent Application P 4 243 705, pyridylpyrimidines, as described, for example, in WO 92/12974, phenylbenzoates, as described, for example, in P. Keller, Ferroelectrics 58 (1984), 3, and J. W. Goodby et al., Liquid Crystals and Ordered Fluids, Vol. 4, New York, 1984, and macrocyclic compounds, as described, for example, in EP-A 0 528 415.

Examples of suitable chiral, non-racemic dopes are:

optically active phenylbenzoates, as described, for example, in P. Keller, Ferroelectrics 58 (1984), 3, and J. W. Goodby et al., Liquid Crystals and Ordered Fluids, Vol. 4, New York, 1984, optically active oxirane ethers, as described, for example, in EP-A 0 263 437 and WO-A 93/13093, optically active oxirane esters, as described, for example, in EP-A 0 292 954, optically active dioxolane ethers, as described, for example, in EP-A 0 351 746, optically active dioxolane esters, as described, for example, in EP-A 0 361 272, and optically active tetrahydrofuran-2-carboxylic esters, as described, for example, in EP-A 0 355 561.

Particularly preferred further components of the mixtures according to the invention are compounds of the formulae III to XVI:

A. Phenylpyrimidines of the formula III

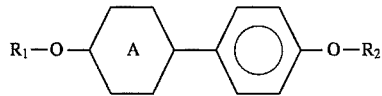

in which:

$R_1$ and $R_2$ are identical or different and are a straight-chain or branched alkyl group having 1 to 18 or 3 to 18 carbon atoms respectively, where a $CH_2$ group adjacent to the oxygen in one of the radicals $R^1$ and $R^2$ may also be replaced by —CO—;

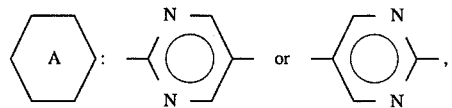

and IV

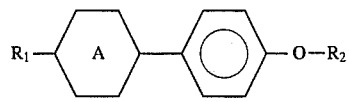

in which:

$R_1$ and $R_2$ are identical or different and are a branched or unbranched alkyl group having 1 to 18 or 3 to 18 carbon atoms respectively, where a $CH_2$ group adjacent to the oxygen may also be replaced by —CO—;

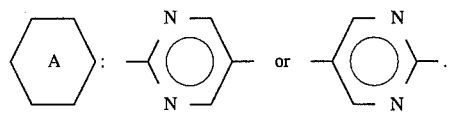

B. Metasubstituted aromatic compounds having a six-membered ring, of the formula V

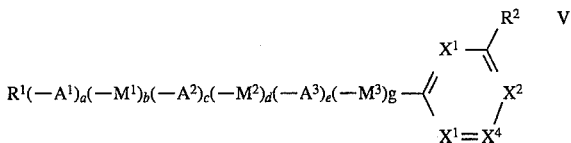

in which $R^1$ and $R^2$ are identical or different, straight-chain or branched alkyl radicals having 1 to 22 or 3 to 22 carbon atoms respectively, where one or two non-adjacent —$CH_2$— groups my also be replaced by —O—, —CO—, —CO—O—, —O—CO—, —O—CO—O— or —Si(CH$_3$)$_2$—;

$A^1$, $A^2$ and $A^3$ are identical or different and are 1,4-phenylene, in which one or two H atoms may be replaced by F, pyridine-2,5-diyl, in which one or two H atoms may be replaced by F, pyrimidine-2,5-diyl, in which one or two H atoms may be replaced by F, trans-1,4-cyclohexylene, in which one or two H atoms may be replaced by —CN and/or —CH$_3$, or 1,3,4-thiadiazole- 2,5-diyl;

and $A^1$ is alternatively

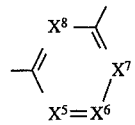

$M^1$, $M^2$ and $M^3$ are identical or different and are —O—, —CO—O—, —O—CO—, —CH$_2$—O—, —O—CH$_2$— or —CH$_2$—CH$_2$—;

$X^1$, $X^2$, $X^3$, $X^4$, $X^5$, $X^6$, $X^7$ and $X^8$ are CH or N, where the number of N atoms per six-membered ring is 0, 1 or 2, and a, b, c, d, e and f are zero or one, with the proviso that the sum a+c+e is 0, 1 or 2.

C. Carbonates of the formula VI

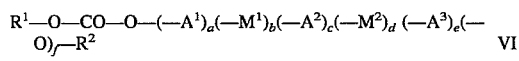

in which $R^1$ and $R^2$ are identical or different and are a straight-chain or branched alkyl group having 1 to 22 or 3 to 22 carbon atoms respectively;

$A^1$, $A^2$ and $A^3$ are identical or different and are 1,4-phenylene, in which one or two H atoms may also be replaced by F, pyrimidine-2,5-diyl, in which one or two H atoms may also be replaced by F, or pyridine-2,5-diyl, in which one or two H atoms may also be replaced by F;

$M^1$ and $M^2$ are identical or different and are —O—, —CO—, —CO—O—, —O—CO—, —CH$_2$—O—, —O—CH$_2$— or —CH$_2$—CH$_2$—;

a, b, c, d, e and f are zero or one, with the proviso that the sum a+c+e is 1, 2 or 3.

D. Silicon compounds of the formula VII $$R^1(-A^1)_i(-M^1)_k(-A_2)_l(-M_2)_m(-A^3)_n-R^2 \quad \text{VII}$$

in which
- $R^1$ is a straight-chain or branched alkyl group having 1 to 22 or 3 to 22 carbon atoms respectively, where one or two non-adjacent —$CH_2$— groups may also be replaced by —O—, —CO—, —CO—O—, —O—CO— or —O—CO—O—;
- $R^2$ is straight-chain or branched alkyl having 1 to 22 or 3 to 22 carbon atoms respectively, where one or two non-adjacent —$CH_2$— groups may also be replaced by —O—, —CO—, —CO—O—, —O—CO— or —O—CO—O—, with the proviso that one $CH_2$ group not bonded to oxygen has been replaced by —$Si(CH_3)_2$—;
- $A^1$, $A^2$ and $A^3$ are identical or different and are 1,4-phenylene, in which one or two H atoms may be replaced by F, trans-1,4-cyclohexylene, pyridine-2,5-diyl, in which one or two H atoms may be replaced by F, pyrimidine-2,5-diyl, in which one or two H atoms may each be replaced by F, or 1,3,4-thiadiazole-2,5-diyl;
- $M^1$ and $M^2$ are identical or different and are —CO—O—, —O—CO—, —$CH_2$—O— or —O—$OH_2$—, and i, k, l, m and n are zero or 1, with the proviso that i+l+n=2 or 3.

E. Hydroquinone derivatives of the formula VIII

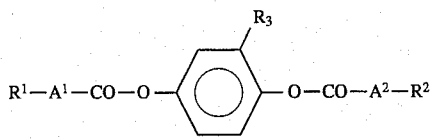

in which
- $R^1$ and $R^2$ are identical or different, straight-chain or branched alkyl radicals having i or 3 to 16, preferably 1 or 3 to 10 carbon atoms respectively, where one or two non-adjacent —$CH_2$— groups may also be replaced by —O—, —CO—, —O—CO—, —CO—O— or —O—CO—O—,
- $R^3$ is —$CH_3$, —$CF_3$ or —$C_2H_5$,
- $A^1$ and $A^2$, independently of one another, are

F. Pyridylpyrimidines of the formula (IX)

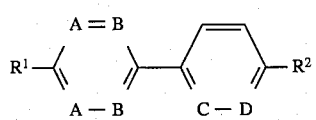

in which
- A is N and B is CH or A is CH and B is N, C is N and D is CH or C is CH and D is N, where one or two CH groups may be replaced by CF groups, and
- $R^1$ and $R^2$ are identical or different, straight-chain or branched alkyl radicals having I to 22 or 3 to 22 carbon atoms respectively, where one or two non-adjacent —$CH_2$— groups may also be replaced by —O—, —CO—, —CO—O—, —O—CO— or —O—CO—O—.

G. Phenylbenzoates of the formula X

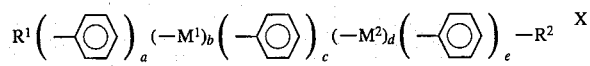

in which
- $R^1$ and $R^2$ are identical or different, straight-chain or branched alkyl radicals having 1 to 22 or 3 to 22 carbon atoms respectively, where one or two non-adjacent —$CH_2$— groups may also be replaced by —O—, —CO—, —CO—O—, —O—CO— or —O—CO—O—;
- $M^1$ and $M^2$ are identical or different and are —CO—O— or —O—CO—, and
- a, b, c, d and e are zero or one, with the proviso that a+c+e=2 or 3 and b+d=1 or 2.

H. Optically active phenylbenzoates of the formula XI

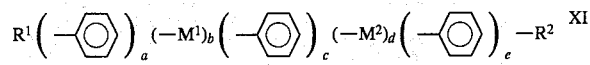

in which
- $R^1$ and $R^2$ are identical or different, straight-chain or branched alkyl radicals having 1 to 22 or 3 to 22 carbon atoms respectively, where one or two non-adjacent —$CH_2$— groups may also be replaced by —O—, —CO—, —CO—O—, —O—CO— or —O—CO—O—, and in which at least one of the radicals $R^1$ and $R^2$ is chiral and non-racemic;
- $M^1$ and $M^2$ are identical or different and are —CO—O—, —O—CO— or a single bond, and
- a, b, c, d and e are zero or one, with the proviso that a+c+e is 2 or 3.

I. Optically active oxirane ethers of the formula XII

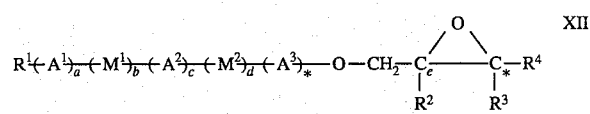

in which the symbols and indices have the following meanings:
- * is a chiral center;
- $R^1$ is a straight-chain or branched alkyl radical having 1 to 22 or 3 to 22 carbon atoms respectively, where one or two non-adjacent —$CH_2$— groups may also be replaced by —O—, —CO—, —CO—O—, —O—CO—, —O—CO—O— or —$Si(CH_3)_2$—, or the following optically active group:

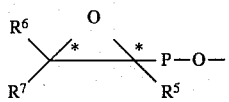

- $R^2$, $R^3$, $R^4$, $R^5$, $R^6$ and $R^7$, independently of one another, are H or a straight-chain or branched alkyl radical having 1 to 16 or 3 to 16 carbon atoms respectively;
- P is —$CH_2$— or —CO—;
- $A^1$, $A^2$ and $A^3$ are identical or different and are 1,4-phenylene, in which one or two H atoms may be replaced by F, pyridine-2,5-diyl, in which one or two H atoms may each be replaced by F, pyrimidine-2,5-diyl, in which one or two H atoms may be replaced by F, trans-1,4-cyclohexylene, in which one or two H atoms may be replaced by —CN and/or —$CH_3$, or 1,3,4-thiadiazole- 2,5-diyl; $M^1$ and $M^2$ are identical or different and are —CO—O—, —O—CO—, —$CH_2$—

O—, —O—CH$_2$— or —CH$_2$—CH$_2$—, and a, b, c, d and e are zero or 1.

J. Optically active oxirane esters of the formula XIII

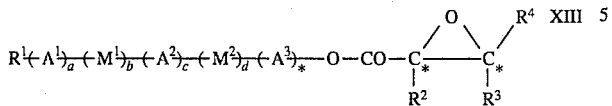

where the symbols and indices have the following meanings:
* is a chiral center;
R$^1$ is a straight-chain or branched alkyl radical having 1 to 22 or 3 to 22 carbon atoms respectively, where one or two non-adjacent —CH$_2$— groups may also be replaced by —O—, —CO—, —CO—O—, —O—CO—, —O—CO—O— or —Si(CH$_3$)$_2$—;
R$^2$, R$^3$ and R$^4$ are identical or different and are H or a straight-chain or branched alkyl radical having 1 to 16 carbon atoms;
A$^1$, A$_2$ and A$^3$ are identical or different and are 1,4-phenylene, in which one or two H atoms may be replaced by F, pyridine-2,5-diyl, in which one or two H atoms may be replaced by F, pyrimidine-2,5-diyl, in which one or two H atoms may be replaced by F, trans-1,4-cyclohexylene, in which one or two H atoms may be replaced by —CN and/or —CH$_3$, or 1,3,4-thiadiazole- 2,5-diyl;
M$^1$ and M$^2$ are identical or different and are —CO—O—, —O—CO—, —CH$_2$—O—, —O—CH$_2$— or —CH$_2$—CH$_2$—;
a, b, c, d and e are zero or one.

K. Optically active dioxolane ethers of the formula XIV

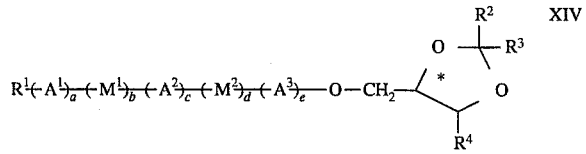

where the symbols and indices have the following meanings:
* is a chiral center;
R$^1$ is a straight-chain or branched alkyl radical having 1 to 22 or 3 to 22 carbon atoms respectively, where one or two non-adjacent —CH$_2$— groups may also be replaced by —O—, —CO—, —CO—O—, —O—CO—, —O—CO—O— or —Si(CH$_3$)$_2$—;
R$^2$, R$^3$ and R$^4$ are identical or different and are H or a straight-chain or branched alkyl radical having 1 to 16 carbon atoms, where R$^2$ and R$^3$ together may alternatively be —(CH$_2$)$_5$—;
A$^1$, A$^2$ and A$^3$ are identical or different and are 1,4-phenylene, in which one or two H atoms may be replaced by F, pyridine-2,5-diyl, in which one or two H atoms may be replaced by F, pyrimidine-2,5-diyl, in which one or two H atoms may be replaced by F, trans-1,4-cyclohexylene, in which one or two H atoms may be replaced by —CN and/or —CH$_3$, or 1,3,4-thiadiazole- 2,5-diyl;
M$^1$ and M$^2$ are identical or different and are —CO—O—, —O—CO—, —CH$_2$—O—, —O—CH$_2$— or —CH$_2$—CH$_2$—, and a, b, c, d and e are zero or one.

L. Optically active dioxolane esters of the formula XV

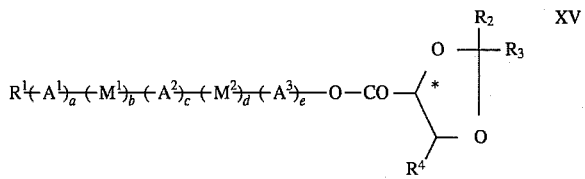

in which
R$^1$ is a straight-chain or branched alkyl radical having 1 to 16 carbon atoms where one or more non-adjacent —CH$_2$- groups may also be replaced by —O—, —CO—, —O—CO— or —CO—O—;
R$^2$, R$^3$ and R$^4$ are identical or different and are H or a straight-chain alkyl radical having 1 to 16 carbon atoms;
A$^1$, A$^2$ and A$^3$ are identical or different and are 1,4-phenylene, in which one or two H atoms may be replaced by F, pyridine-2,5-diyl, in which one or two H atoms may be replaced by F, pyrimidine-2,5-diyl, in which one or two H atoms may be replaced by F, trans-1,4-cyclohexylene, in which one or two H atoms may be replaced by —CN and/or —CH$_3$, or 1,3,4-thiadiazole- 2,5-diyl;
M$^1$ and M$^2$ are identical or different and are —CO—O—, —O—CO—, —CH$_2$—O—, —O—CH$_2$— or —CH$_2$—CH$_2$—, and a, b, c, d and e are zero or one.

M. Macrocyclic compounds of the formula XVI

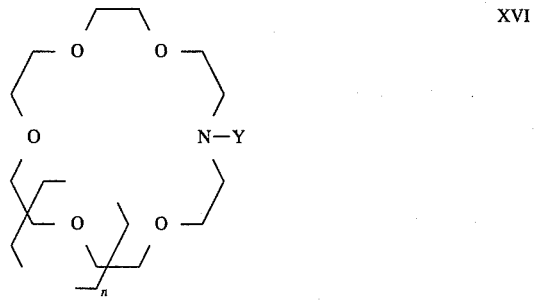

where
n is 0 or 1, and
Y is —CO— (t-butyl) or —CO— (adamantyl).

The mixtures according to the invention are suitable for use in all areas of optical technology, for example in switching and display elements (displays), light valves and components having NLO properties. The mixtures according to the invention are particularly suitable for use where the properties of smectic liquid crystals are utilized.

However, since the mixtures generally also form nematic phases, use in the area of nematics technology is in principle also possible. Achiral base mixtures can be used in all areas in which anisotropic fluids are employed, for example as column materials for gas chromatography.

Ferroelectric mixtures according to the invention are preferably used in the FLC cells described in the introduction, which are based on the utilization of the SSFLC effect (see, for example, J. W. Goodby et al., Ferroelectric Liquid Crystals, 24 ff., Gordon & Breach, Philadelphia, 1991).

In these cells, the compounds according to the invention are preferably employed in combinations with alignment layers, as proposed, for example, in DE 42 12 893 or in the German patent application with the title "Cyclische Strukturelemente enthaltende Silan-Koppler als Orientierungrungsschichten" [Silane couplers containing cyclic structural elements as alignment layers], where an alignment film for liquid crystals is described which comprises a quasi-monomolecular layer of compounds of the formula XVII $$C_y\text{-}S_p\text{-}A_n \qquad \text{XVII}$$

in which $C_y$ is a mediocyclic or macrocyclic carbon ring having 8 or more ring members, where this ring may also contain fused benzene rings and —O—, —N—, —S—, —Si— and —B— as hetero atoms;

$S_p$ is an alkyl group having 1 to 20 carbon atoms in which one or more non-adjacent —CH$_2$— groups may be replaced by —O—, —S—, —CO—, —O—CO—, —NH—CO—, —O—COO—, —NH—CO—NH—, —NH—CO—O—, —SO$_2$—, —Si (CH$_3$)$_2$—, —CH=CH— or —C≡C—;

$A_n$ is $SiX^1X^2X^3$, where $X^1$ is a single bond and $X^2$ and $X^3$, independently of one another, are a single bond, an alkyl group or an alkoxy group;

where the compounds are bonded to an oxygen-containing layer via the single bond(s) of group $A_n$.

The mixtures according to the invention are furthermore suitable for field treatment, i.e. for operation in the quasi-bookshelf geometry (QBG) (see, for example, H. Rieger etal., SID 91 Digest (Anaheim), 1991, p. 396).

The mixtures according to the invention are likewise suitable for use in ferroelectric liquid-crystal displays which are based on utilization of the DHF effect or the PSFLCD effect (pitch stabilized ferroelectric liquid-crystal display, also known as SBF, short pitch bistable ferroelectric effect). The DHF effect is described, for example, by B. I. Ostrovski in Advances in Liquid Crystal Research and Applications, Oxford/Budapest, 1980, 469 ff., and the PSFLCD effect is described, for example, in DE-A 3 920 625 and EP-A 0 405 346. Utilization of this effect requires, in contrast to the SSFLC effect, a liquid-crystalline material having a short $S_C$ pitch.

The invention is described in greater detail by means of the examples, but this is not intended to represent a limitation.

EXAMPLES

Various measurement methods were used to physically characterize the mixtures according to the invention.

The phase-transition temperatures were determined from the changes in structure on heating with the aid of a polarizing microscope. The melting point was determined using a DSC instrument. The phase-transition temperature data between the phases

| isotropic | (I) |
| nematic | (N or N*) |
| smectic C | ($S_C$ or $S_C$*) |
| smectic A | ($S_A$) |
| crystalline | (X) | are given in ° C., and the values are between the phase designations in the phase sequence. Values in parentheses were obtained on cooling.

In order to determine the electro-optical properties of the mixtures, self-made 1-pixel test cells having alignment layers as described above are used. The thickness of the liquid crystal layer varies between 1.5 and 2 μm. The cells are filled by means of capillary forces in the isotropic phase with or without vacuum. The CPA measurements were carried out using the electrical addressing scheme shown in SPIE 1665, Liquid Crystal Materials, Devices and Applications (1992) with a bias B=4:1. The margin measurements were carried out using the addressing scheme shown in the same citation with a bias B=4:1, where the percentage margin given relates to the threshold voltage measured using the same scheme.

Example 1

A mixture M1 according to the invention having the constituents:

| Structure | % by weight |
|---|---|
| $C_6H_{13}$—CO—O—[pyrimidine]—[phenyl]—O—CO—$C_7H_{17}$ | 6.2 |
| $C_8H_{17}$—O—[phenyl]—[pyrimidine]—O—CO—[phenyl]—H | 5.71 |
| $C_7H_{15}$—O—[pyrimidine]—[phenyl]—O—$C_9H_{19}$ | 6.4 |
| $C_6H_{13}$—O—[pyrimidine]—[phenyl]—O—$C_8H_{17}$ | 7.23 |
| $C_8H_{17}$—[pyrimidine]—[phenyl]—O—$C_{10}H_{21}$ | 6.98 |

-continued
| | % by weight |
|---|---|
| 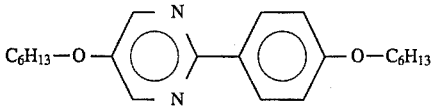 | 5.02 |
| 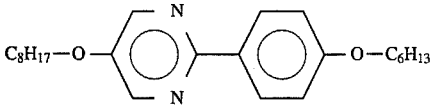 | 7.23 |
| 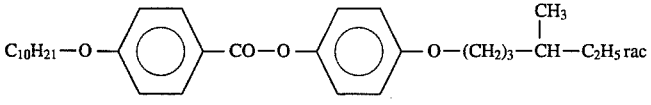 | 7.71 |
| 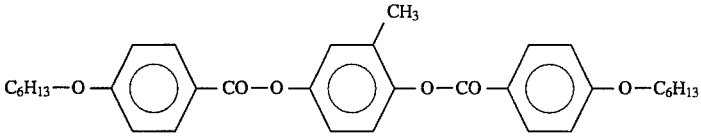 | 2.5 |
| 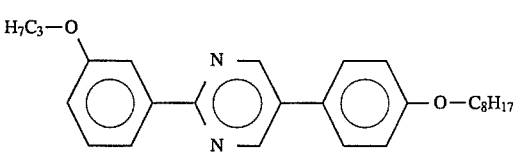 | 7.87 |
| 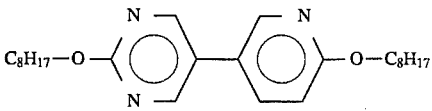 | 4.85 |
| 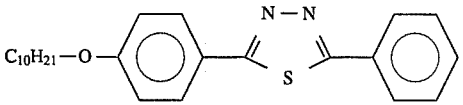 | 6.49 |
| 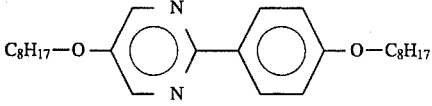 | 7.76 |
| 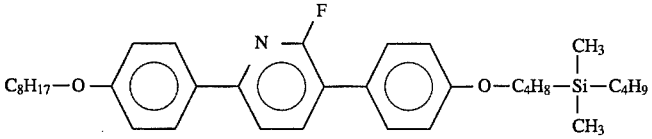 | 4.89 |
| 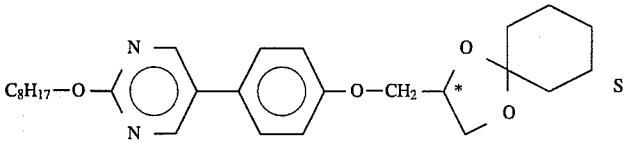 | 1.63 |
| 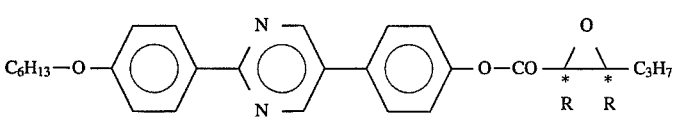 | 6.61 |
| 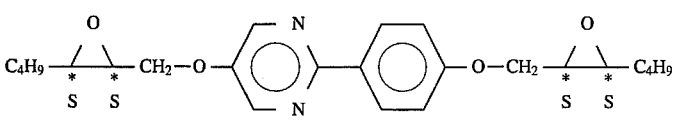 | 4.93 |
has the following phase ranges: X–16 (–35) $S_C^*$ 71 $S_A$ 86 $N^*$ 93 I.

Example 2
A mixture M2 according to the invention having the constituents:
| | % by weight |
|---|---|
| 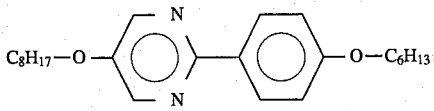 | 11.07 |
| 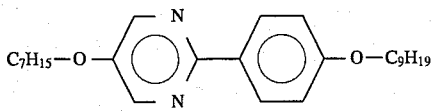 | 5.48 |
| 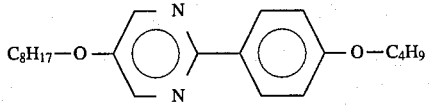 | 10.82 |
| 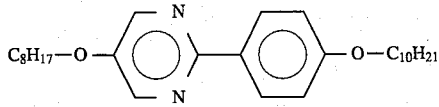 | 10.63 |
| 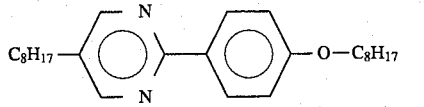 | 5.78 |
| 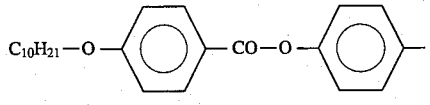 | 7.49 |
| 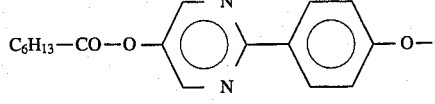 | 6.03 |
| 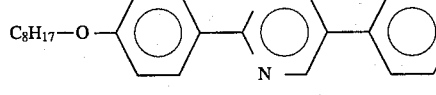 | 6.03 |
| 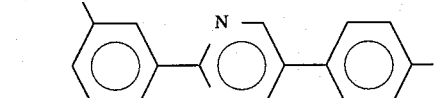 | 5.62 |
| 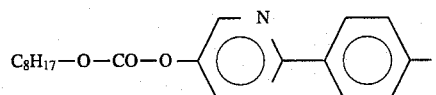 | 8.42 |
| 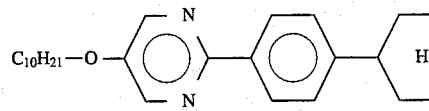 | 7.05 |
| 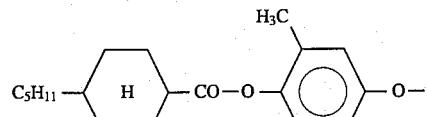 | 9.20 |

| | % by weight |
|---|---|
| C₄H₉—[epoxide*S,S]—CH₂—O—[pyrimidine]—[phenyl]—O—CH₂—[epoxide*S,S]—C₄H₉ | 2.32 |
| C₆H₁₃—O—[phenyl]—[pyrimidine]—[phenyl]—O—CO—[epoxide*R,R]—C₃H₇ | 2.38 |
| C₄H₉—[epoxide*S,S]—CH₂—O—[pyrimidine]—[phenyl]—O—CO—[cyclohexyl H]—C₅H₁₁ | 1.68 | has the following phase ranges:

X –16.5 (–35) $S_C^*$ 71 $S_A$ 86 $N^*$ 98 I.

Example 3

A comparative mixture V1 contains six phenylpyrimidine derivatives, as described in WO 86/06401. The total of the concentrations of these six compounds is 43.7 mol %. Addition of 4-(5-heptanoyloxypyrimidin-2-yl)phenyl nonanoate (compound of the formula I) to this mixture gives mixture M3 according to the invention. It can be seen from Table 1 that the mixture according to the invention has a lower melting point and a broad $S_C^*$ phase range.

In M3, the total of the concentrations of the six compounds disclosed in WO 86/06401 and the compound according to the invention is 46.6 mol %.

Comparative mixture V2 has qualitatively the same composition as V1 but the total of the concentration of the six compounds disclosed in WO 86/06401 is 46.6 mol % in comparison to 43.7 mol % in V1.

Therefore in V2 the total of the concentration of the six compounds disclosed in WO86/06401 is the same as is the total of the concentration of said six compounds and the compound according to the invention in M3.

Table 1 shows that the mixture M3 according to the invention also has a significantly improved melting point and $S_C^*$ phase range compared with V2.

TABLE 1

Comparison of the phase ranges of M3 with two comparative mixtures

| X | $S_C^*$ | $S_A^*$ | N | I |
|---|---------|---------|-----|-------|
| V1 | −19 (−36) | 67 | 89 | 91–93 |
| M3 | −20 (−39) | 71 | 86 | 91–93 |
| V2 | −15 (−39) | 71 | 75 | 89–91 |

(values in parentheses on cooling)

Comparative mixture 1 (V1)

| Structure | % by weight |
|---|---|
| $C_8H_{17}$—[pyrimidine]—[phenyl]—O—$C_{10}H_{21}$ | 7.50 |
| $C_6H_{13}$—O—[pyrimidine]—[phenyl]—O—$C_6H_{13}$ | 5.40 |
| $C_6H_{13}$—O—[pyrimidine]—[phenyl]—O—$C_8H_{17}$ | 7.78 |
| $C_7H_{15}$—O—[pyrimidine]—[phenyl]—O—$C_9H_{19}$ | 6.89 |
| $C_8H_{17}$—O—[pyrimidine]—[phenyl]—O—$C_6H_{13}$ | 7.78 |
| $C_8H_{17}$—O—[pyrimidine]—[phenyl]—O—$C_8H_{17}$ | 8.34 |
| [cyclohexyl]—[phenyl]—CO—O—[pyrimidine]—[phenyl]—O—$C_8H_{17}$ | 6.15 |
| $C_8H_{17}$—O—[pyridine]—[pyridine]—O—$C_8H_{17}$ | 5.23 |
| $C_3H_7$—O—[phenyl]—[pyrimidine]—[phenyl]—O—$C_8H_{17}$ | 6.46 |
| $C_5H_{11}$—[cyclohexyl]—[phenyl]—[fluoropyridine]—O—$C_4H_8$—Si(CH$_3$)$_2$—$C_4H_9$ | 6.12 |
| $C_{10}H_{21}$—O—[phenyl]—CH=N—N=CH—[phenyl] (with S) | 6.98 |

TABLE 1-continued
Comparison of the phase ranges of M3 with two comparative mixtures
| Structure | % by weight |
|---|---|
| 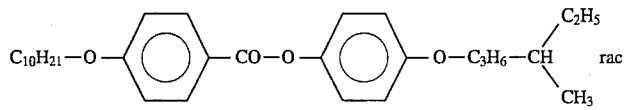 | 8.28 |
| 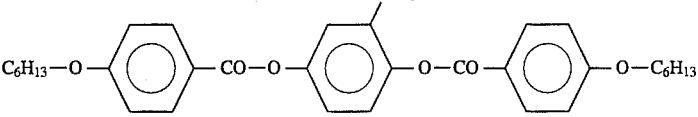 | 2.69 |
| 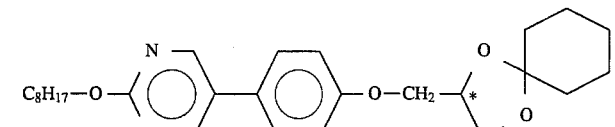 | 2.18 |
| 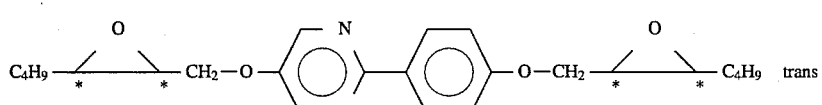 | 2.96 |
| 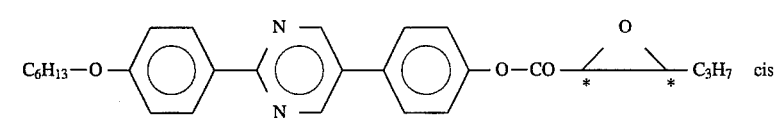 | 7.27 |
M3
| Structure | % by weight |
|---|---|
| 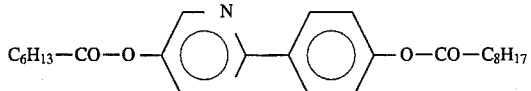 | 6.17 |
| 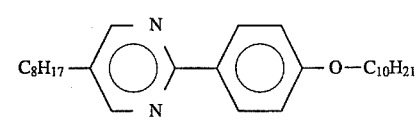 | 6.95 |
| 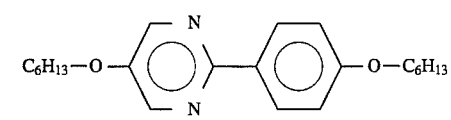 | 4.99 |
| 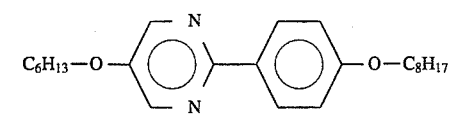 | 7.19 |
| 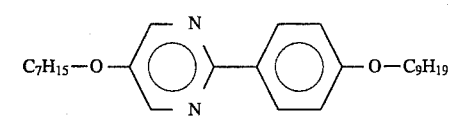 | 6.37 |
| 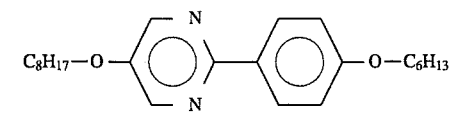 | 7.19 |
| 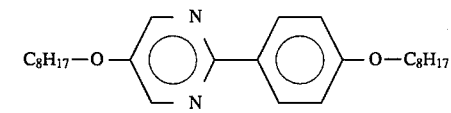 | 7.72 |

TABLE 1-continued

Comparison of the phase ranges of M3 with two comparative mixtures

| Structure | % |
|---|---|
| H–[Cy]–[Ph]–CO–O–[Pyr(N,N)]–[Ph]–O–C$_8$H$_{17}$ | 5.69 |
| C$_8$H$_{17}$–O–[Pyr(N,N)]–[Pyr(N,N)]–O–C$_8$H$_{17}$ | 4.84 |
| C$_3$H$_7$–O–[Ph]–[Pyr(N,N)]–[Ph]–O–C$_8$H$_{17}$ | 7.83 |
| C$_5$H$_{11}$–H–[Cy]–[Ph]–[Pyr(N,F)]–O–C$_4$H$_8$–Si(CH$_3$)$_2$–C$_4$H$_9$ | 6.10 |
| C$_{10}$H$_{21}$–O–[Ph]–C(=N–N)–S–[Ph] | 6.46 |
| C$_{10}$H$_{21}$–O–[Ph]–CO–O–[Ph]–O–C$_3$H$_6$–CH(C$_2$H$_5$)(CH$_3$)  rac | 7.67 |
| C$_6$H$_{13}$–O–[Ph]–CO–O–[Ph(CH$_3$)]–O–CO–[Ph]–O–C$_6$H$_{13}$ | 2.49 |
| C$_8$H$_{17}$–O–[Pyr(N,N)]–[Ph]–O–CH$_2$–*CH–(O–Cy–O) | 2.17 |
| C$_4$H$_9$–*[oxirane]*–CH$_2$–O–[Pyr(N,N)]–[Ph]–O–CH$_2$–*[oxirane]*–C$_4$H$_9$   trans | 2.95 |
| C$_6$H$_{13}$–O–[Ph]–[Pyr(N,N)]–[Ph]–O–CO–*[oxirane]*–C$_3$H$_7$   cis | 7.24 |

| Comparative mixture 2 (V2) | |
|---|---|
| Structure | % by weight |
| C$_8$H$_{17}$–[Pyr(N,N)]–[Ph]–O–C$_{10}$H$_{21}$ | 8.45 |

TABLE 1-continued

Comparison of the phase ranges of M3 with two comparative mixtures

| Structure | Value |
|---|---|
| 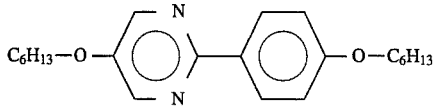 C$_6$H$_{13}$—O—[pyrimidine]—[phenyl]—O—C$_6$H$_{13}$ | 5.88 |
| 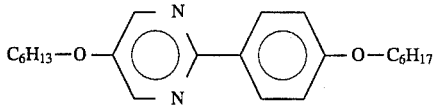 C$_6$H$_{13}$—O—[pyrimidine]—[phenyl]—O—C$_6$H$_{17}$ | 8.15 |
| C$_7$H$_{15}$—O—[pyrimidine]—[phenyl]—O—C$_9$H$_{19}$ | 7.22 |
| C$_8$H$_{17}$—O—[pyrimidine]—[phenyl]—O—C$_6$H$_{13}$ | 8.15 |
| C$_8$H$_{17}$—O—[pyrimidine]—[phenyl]—O—C$_8$H$_{17}$ | 8.75 |
| [cyclohexyl]-H-[phenyl]-CO-O-[pyrimidine]-[phenyl]-O-C$_8$H$_{17}$ | 5.74 |
| C$_8$H$_{17}$—O—[pyrimidine]—[pyrimidine]—O—C$_8$H$_{17}$ | 4.88 |
| C$_3$H$_7$—O—[phenyl]—[pyrimidine]—[phenyl]—O—C$_8$H$_{17}$ | 7.89 |
| C$_5$H$_{11}$—[cyclohexyl]-H-[phenyl]-[F-pyridyl]-O-C$_4$H$_8$-Si(CH$_3$)$_2$-C$_4$H$_9$ | 6.15 |
| C$_{10}$H$_{21}$—O—[phenyl]—[thiadiazole N=N]—[phenyl] | 6.51 |
| C$_{10}$H$_{21}$—O—[phenyl]—CO-O—[phenyl]—O—C$_3$H$_6$—CH(C$_2$H$_5$)(CH$_3$) rac | 7.29 |
| C$_6$H$_{13}$—O—[phenyl]—CO-O—[methylphenyl]—O-CO—[phenyl]—O—C$_6$H$_{13}$ | 2.49 |

TABLE 1-continued

Comparison of the phase ranges of M3 with two comparative mixtures

| Structure | Value |
|---|---|
| C₈H₁₇—O—[pyrimidine]—[phenyl]—O—CH₂—*CH—[dioxolane with cyclohexyl] | 2.18 |
| C₄H₉—*—*—CH₂—O—[pyrimidine]—[phenyl]—O—CH₂—*—*—C₄H₉  trans | 2.97 |
| C₆H₁₃—O—[phenyl]—[pyrimidine]—[phenyl]—O—CO—*—*—C₃H₇  cis | 7.30 |

Example 4

As already shown in Example 3, the substance of the formula I according to the invention has very high solubility and has an extremely positive effect on the phase behavior and the melting point. The mixtures according to the invention allow the number of compounds of the, formulae I, III and IV in the mixture to be significantly reduced, although WO 86/06401 states that at least 3 of these compounds are necessary for the preparation of suitable mixtures.

Comparative mixture 3 (V3) contains only 1 substance as per WO 86/06401. It has a good melting point, but an unsatisfactory $S_C/S_A$ phase transition. While maintaining the dope concentration, firstly the substance of the formula I according to the invention from Example 3 and secondary a eutectic ternary bisalkoxyphenylpyrimidine mixture (see WO 86/06401) are admixed to the extent of 15 mol %, giving mixtures M4 and V4.

The phase sequences of the substance according to the invention and of the eutectic comparative mixture are:

Substance of the formula I from Example 1:

X 63 (35) $S_C$ 81 N 89 I

Eutectic mixture as per WO 86/06401:

X 21 $S_C$ 84 $S_A$ 94 N 97 I

Comparative mixture 3 (V3) has the following phase ranges:

X–39 $S_C^*$ 60 $S_A$ 85 N* 81–89 I

Mixture, M4 according to the invention is obtained from this mixture by addition of 15 mol % of 4-(heptanoyloxypyrimidin-2-yl)phenyl nonanoate. M4 has the following phase ranges:

X–39 $S_C^*$ 69 $S_A$ 79 N* 84–88 I

The mixture according to the invention has a significantly broader $S_C^*$ phase range.

Addition of 18 mol % of a ternary eutectic mixture of bisalkoxyphenylpyrimidines to V3 gives comparative mixture V4.

This has the following phase rangess

X–36 $S_C^*$ 66 $S_A$ 87 N* 80–92 I

The mixture according to the invention has a broader $S_C^*$ phase range and a lower melting point. This is all the more amazing as the hisester of the formula I according to the invention has per se a significantly higher melting point and a significantly smaller $S_C$ phase range than the ternary eutectic mixture present in V4:

| Structure | % by weight |
|---|---|
| Comparative mixture (V3) | |
| C₆H₁₃—O—[pyrimidine]—[phenyl]—O—C₆H₁₃ | 12.59 |
| C₁₀H₂₁—O—[phenyl]—[thiadiazole N–N]—[phenyl] | 7.00 |
| C₁₀H₂₁—O—[phenyl]—CO—O—[phenyl]—O—C₃H₆—CH(C₂H₅)(CH₃)  rac | 28.23 |

| Structure | % by weight |
|---|---|
| 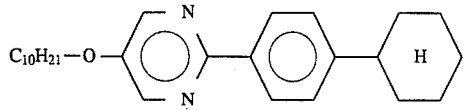 C₁₀H₂₁—O—[pyrimidine]—[phenyl]—[cyclohexyl]—H | 23.58 |
| 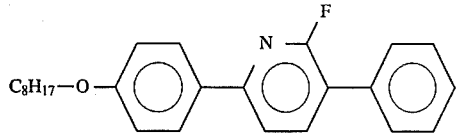 C₈H₁₇—O—[phenyl]—[pyridine(F)]—[phenyl] | 2.51 |
| C₈H₁₇—O—[phenyl]—[pyridine(F,F)]—[phenyl]—O—C₈H₁₇ | 9.29 |
| C₈H₁₇—O—[pyrimidine]—[phenyl]—O—CO—[epoxide*,*]—C₃H₇ cis | 3.16 |
| C₈H₁₇—O—[pyrimidine]—[phenyl]—O—CO—[*]—[dioxolane C(CH₃)₂] | 3.08 |
| C₄H₉—[epoxide*,*]—CH₂—O—[pyrimidine]—[phenyl]—O—CH₂—[epoxide*,*]—C₄H₉ trans | 6.41 |
| C₆H₁₃—O—[phenyl]—[pyrimidine]—[phenyl]—O—CO—[epoxide*,*]—C₃H₇ cis | 3.35 |
| 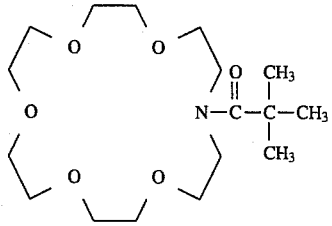 Crown ether—N—C(=O)—C(CH₃)₃ | 0.80 |

M4

| Structure | % by weight |
|---|---|
| C₆H₁₃—O—[pyrimidine]—[phenyl]—O—C₆H₁₃ | 10.32 |
| C₁₀H₂₁—O—[phenyl]—C(=N—N=)—S—[phenyl] | 5.74 |
| C₁₀H₂₁—O—[phenyl]—CO—O—[phenyl]—O—C₃H₆—CH(C₂H₅)(CH₃) rac | 23.14 |

-continued
| Structure | % by weight |
|---|---|
| 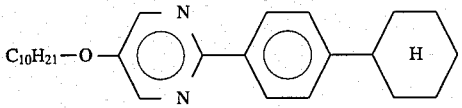 | 19.33 |
| 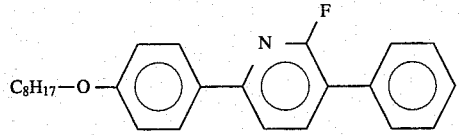 | 2.06 |
| 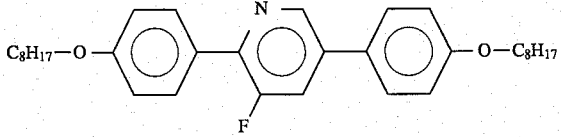 | 7.62 |
| 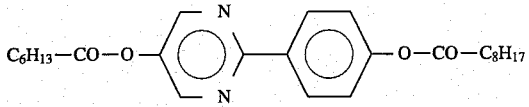 | 15.00 |
| 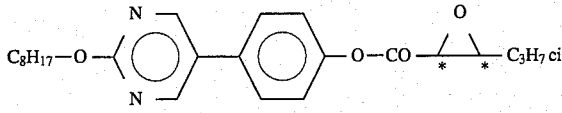 | 3.16 |
| 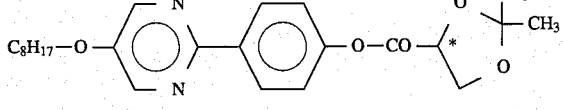 | 3.08 |
| 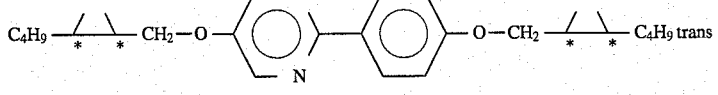 | 6.41 |
| 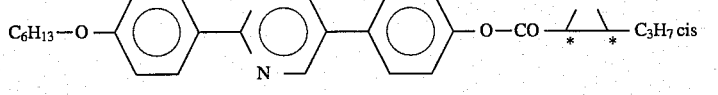 | 3.35 |
| 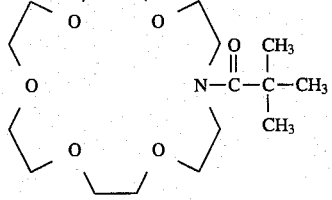 | 0.80 |
Comparative mixture 4 (V4)
| | |
|---|---|
| 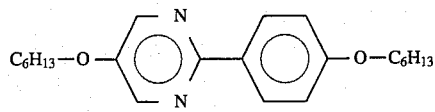 | 10.32 |
| 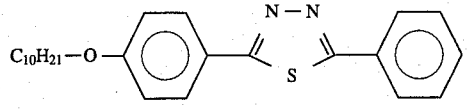 | 5.74 |

| Structure | % by weight |
|---|---|
| 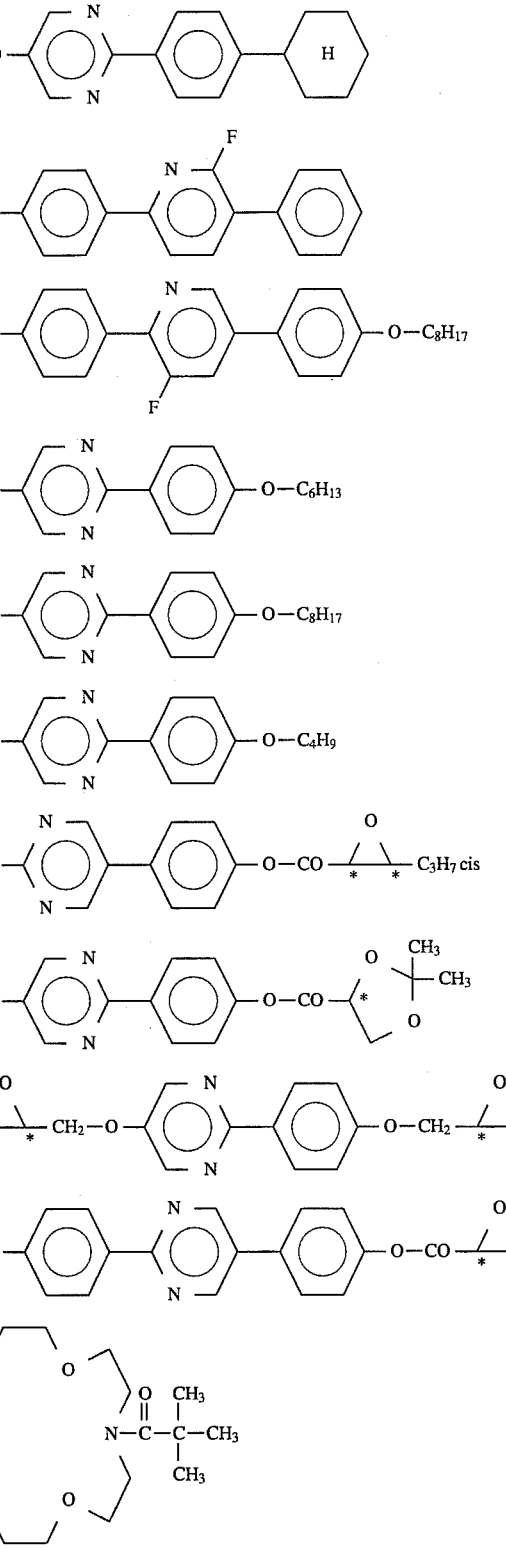 | 23.14 |
| 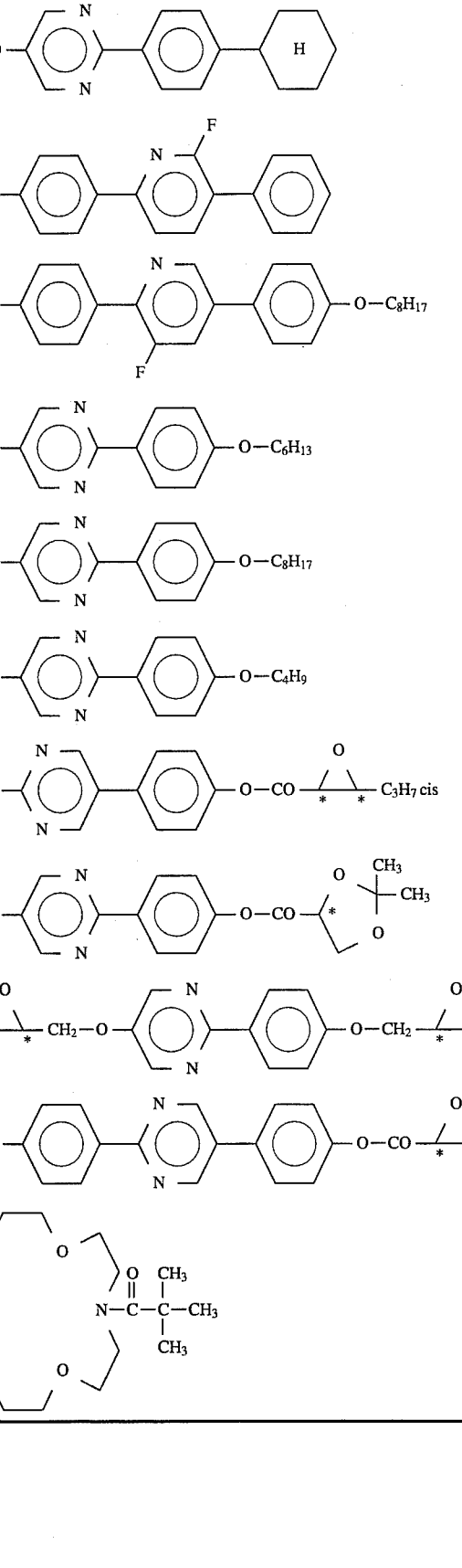 | 19.33 |
| 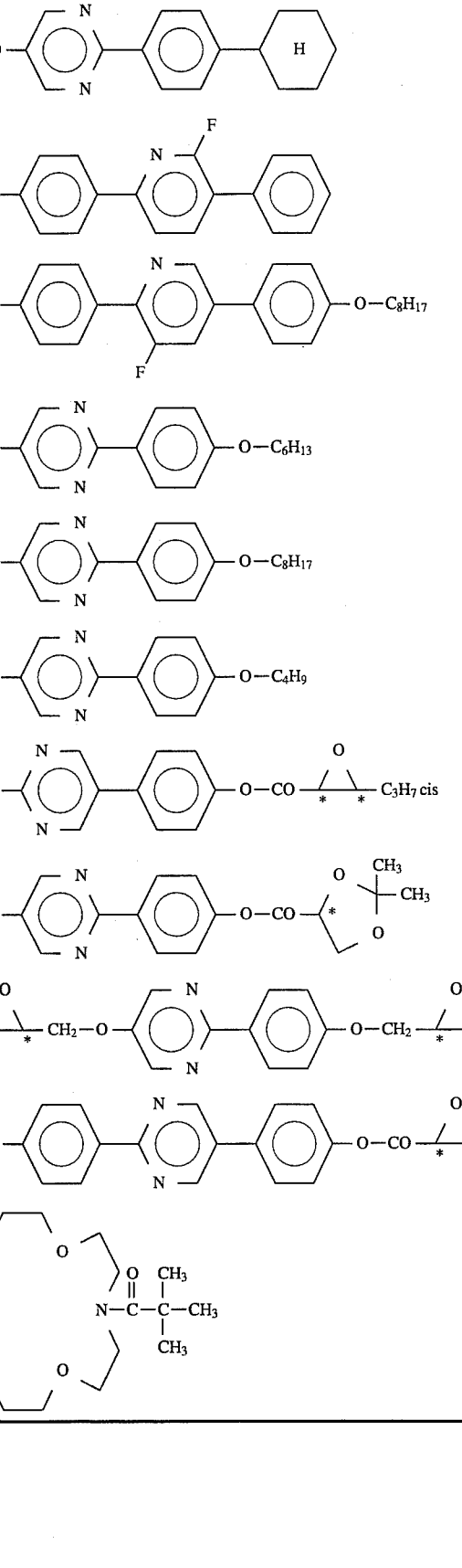 | 2.06 |
| 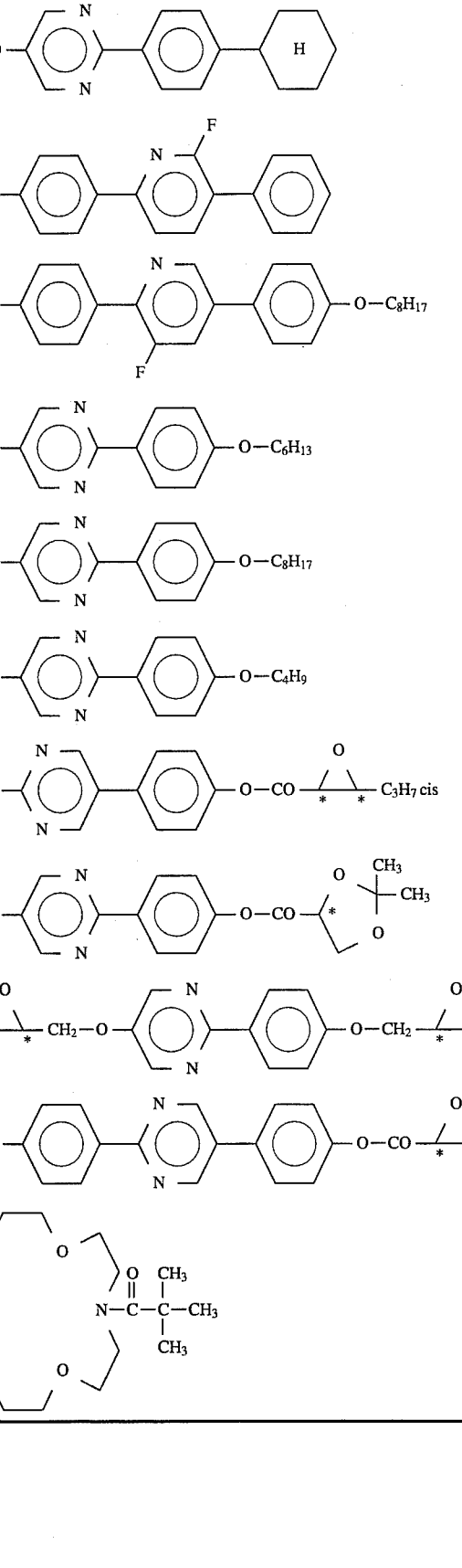 | 7.62 |
| 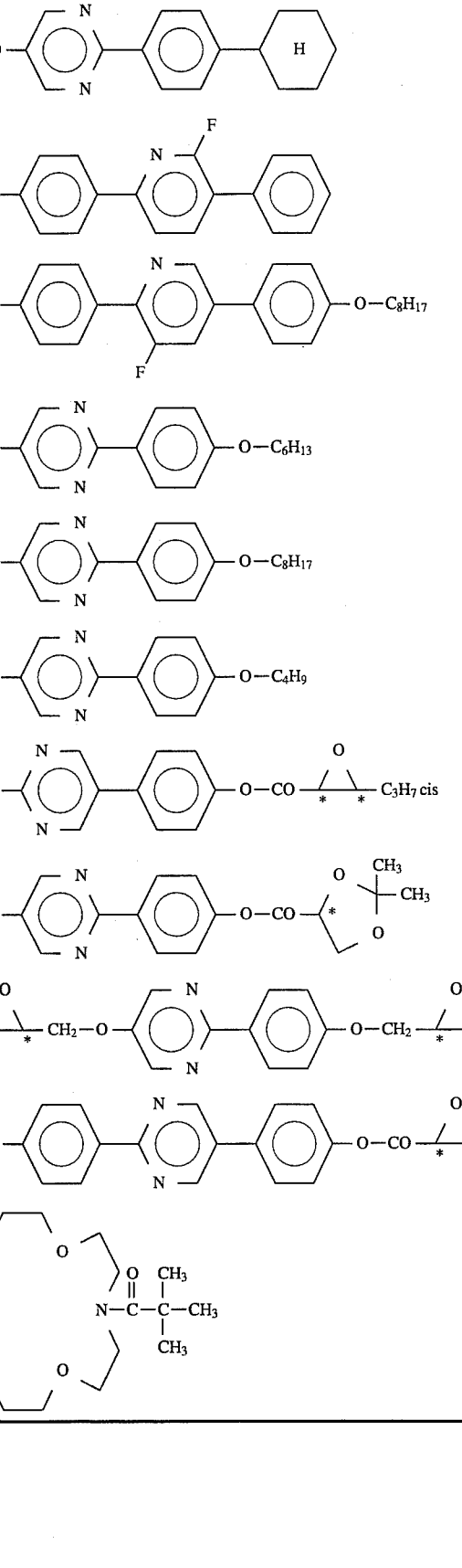 | 6.06 |
| 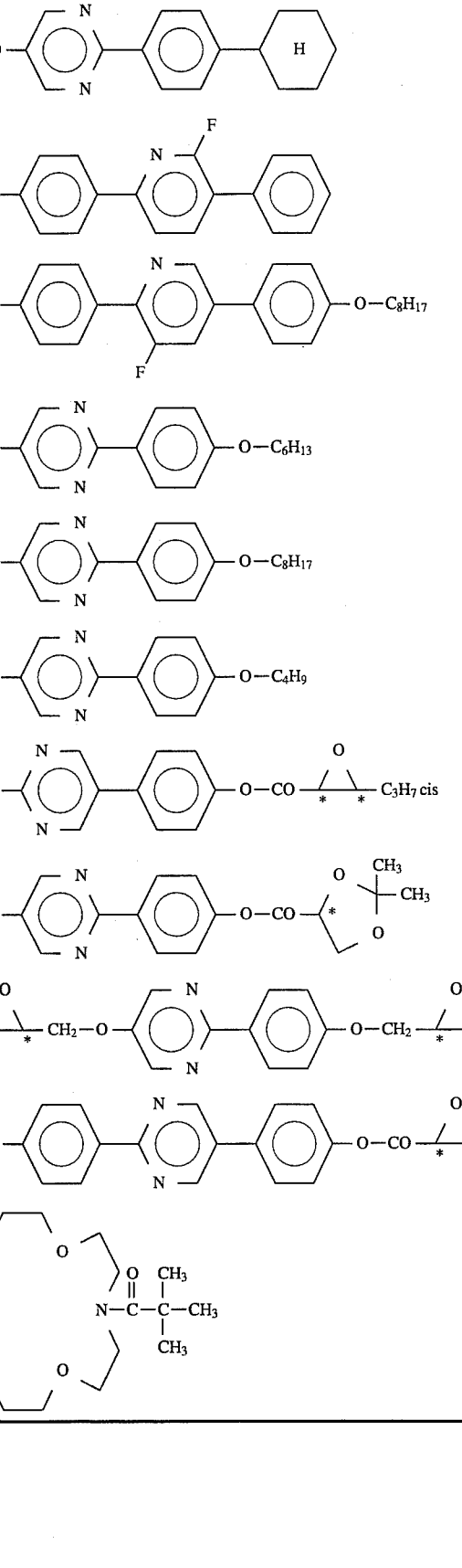 | 4.33 |
| 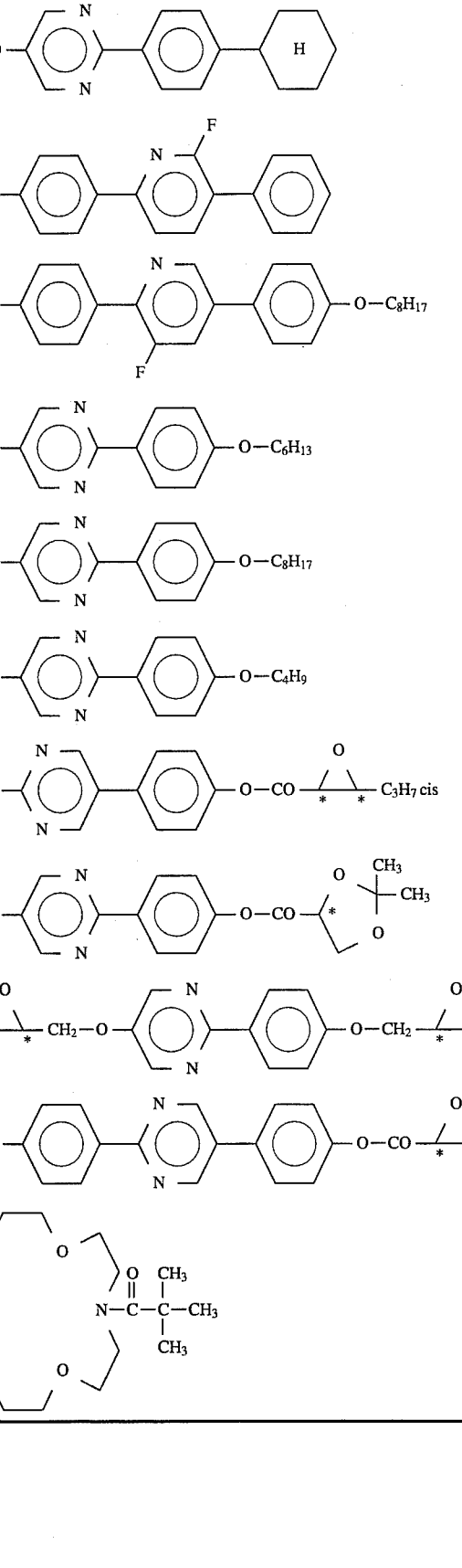 | 4.61 |
| 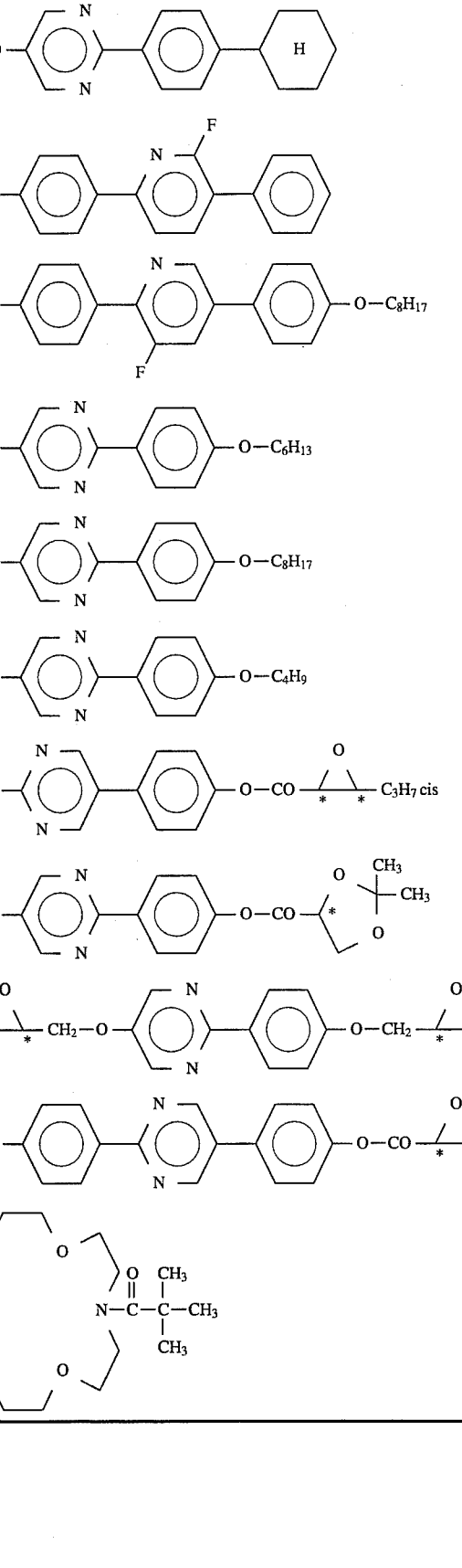 | 3.16 |
| 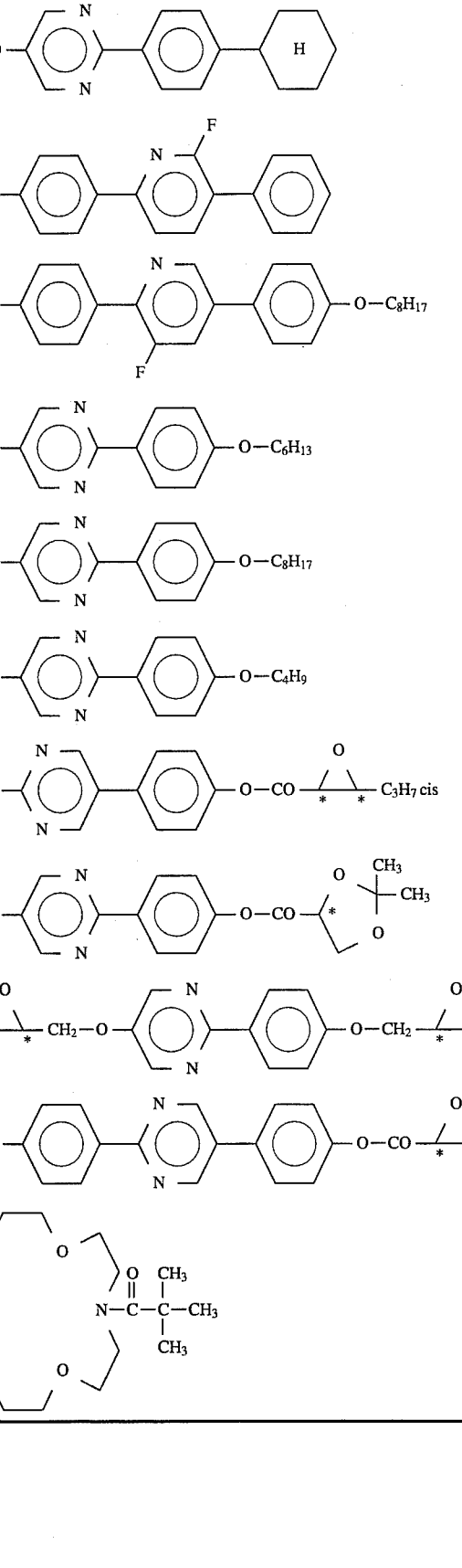 | 3.08 |
| 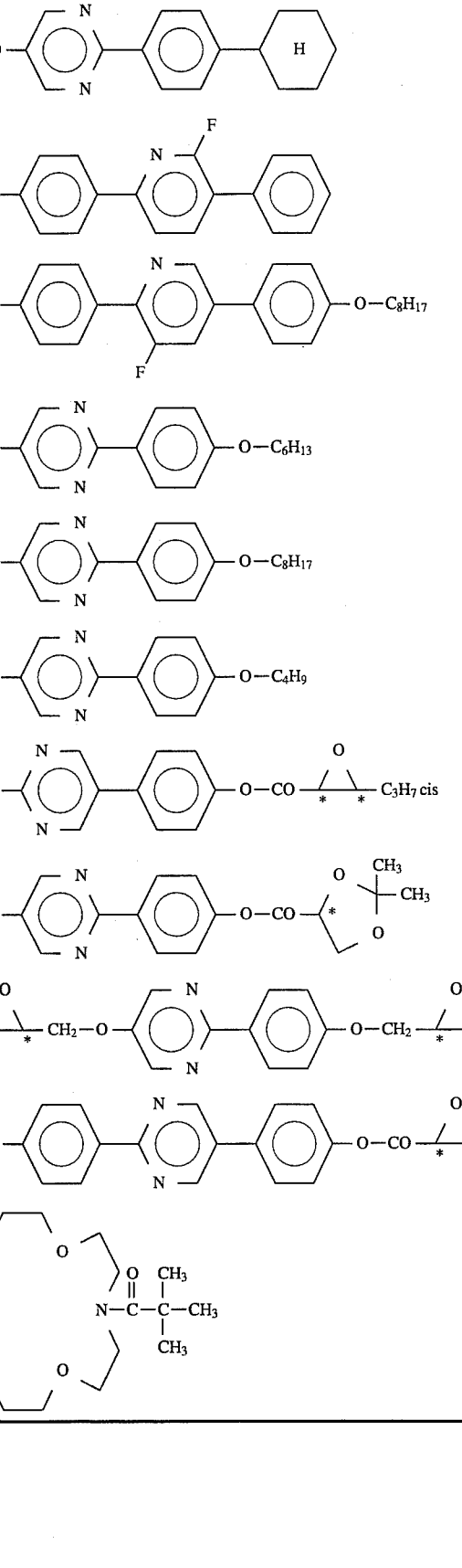 | 6.41 |
| 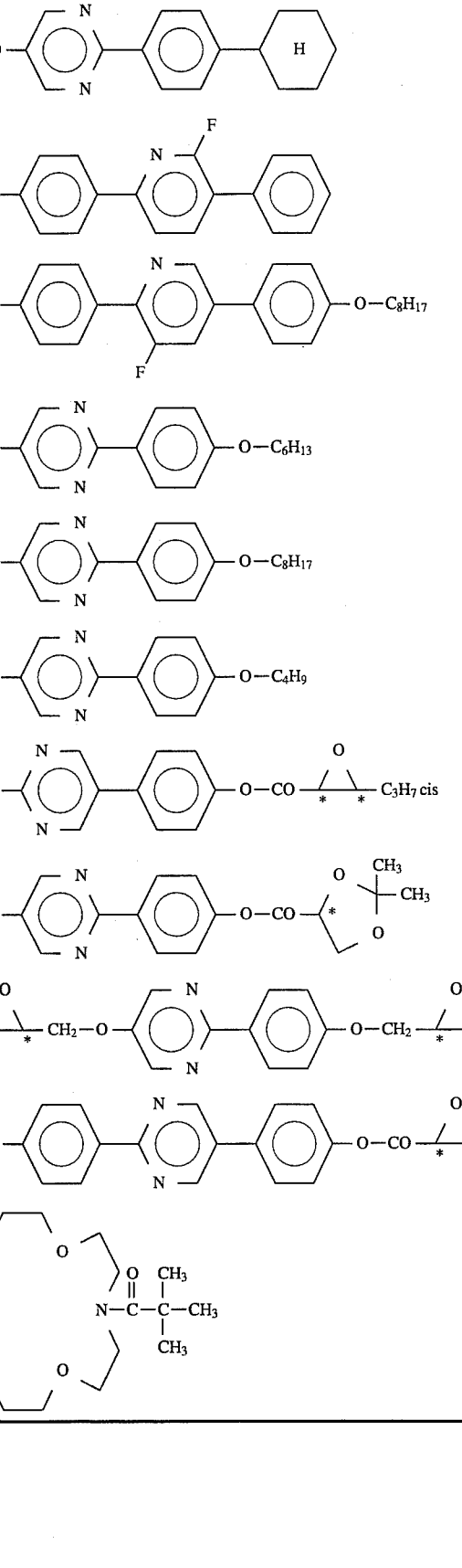 | 3.35 |
| 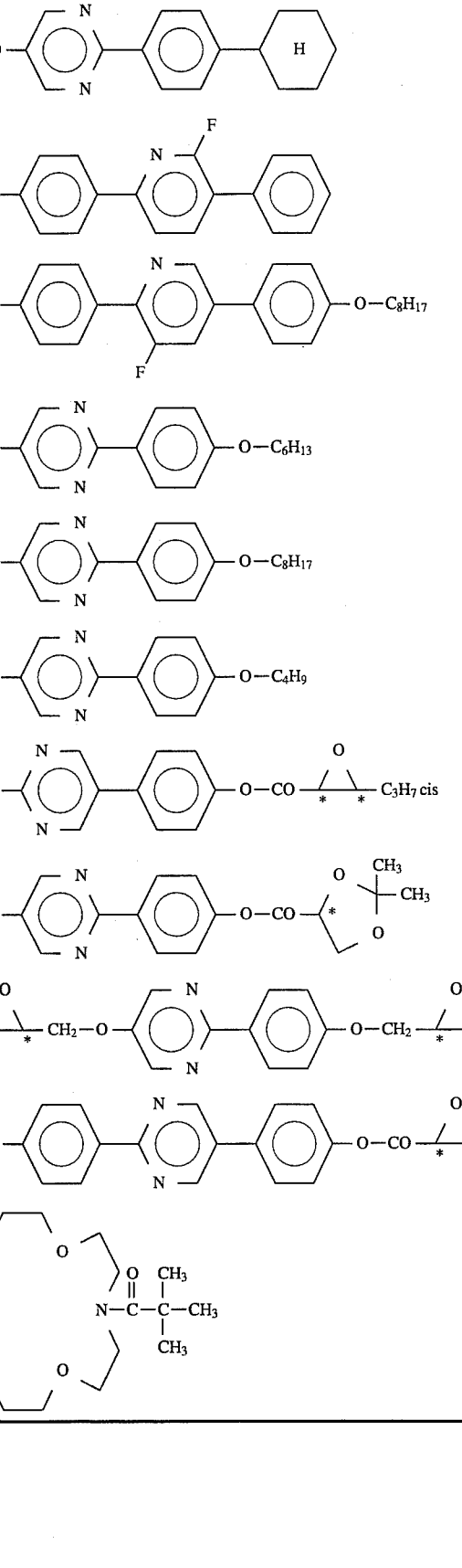 | 0.80 |

TABLE 2

| | | Comparison of the mixture properties at 25° C. | | | | | | |
| --- | --- | --- | --- | --- | --- | --- | --- | --- |
| | | Switching angle° | | η/Pas | | cpa (50μ)/ $Vsm^{-1}$ | | rel. Margin | |
| | Ps/ [$nCcm^{-2}$] | Structure I | Structure IV | Structure I | Structure IV | Structure I | Structure IV | Structure I | Structure IV |
| V3 | 50 | 24 | 41 | 3.24 | 2.08 | *280 | *510 | 0.3 | 0.4 |
| X − 39 $S_c$* 60 $S_A$ N* 82–89 I | | | | | | | | | |
| X4 | 61 | 28.5 | 52 | 2.62 | 1.81 | *260 | *570 | 0.75 | 0.75 |
| X −39 $S_c$* 69 $S_A$ 79 N* 84–88 I | | | | | | | | | |
| V4 | 59 | 25 | 45 | 2.90 | 1.94 | *230 | *480 | 0.25 | 0.3 |
| X −36 $S_c$* 66 $S_A$ 87 N* 80–92 I | | | | | | | | | |

Structure I: chevron geometry
Structure IV: quasi-bookshelf geometry

As can be seen from Table 2, the switching angle in structure I for mixture M4 according to the invention is positively increased and nevertheless the CPA is reduced compared with V3, with a simultaneous significant increase in the relative margin. Although comparative mixture V4 has a lower CPA, this is attributable to the significantly lower switching angle. However, the margin and rotation viscosity of V4 are significantly worse than in M4.

We claim:

1. A liquid-crystal mixture comprising
   a) at least one bisester of the formula I

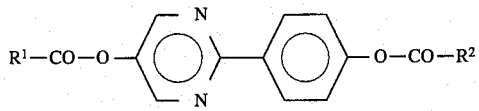

in which
   $R^1$ and $R^2$ are identical or different and are unbranched or branched alkyl chains having 1 or 3 to 20 carbon atoms in which, in addition, one or more H atoms may be replaced by fluorine, and
   b) at least one compound having only one side chain of the formula II

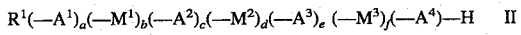

in which
   $R^1$ is a straight-chain or branched alkyl radical having 1 to 22 or 3 to 22 carbon atoms respectively, where one or two non-adjacent —$CH_2$— groups may also be replaced by —O—, —CO—, —CO—O—, —O—CO—, —O—CO—O— or —Si($CH_3$)$_2$—;
   $A^1$, $A^2$, $A^3$ and $A^4$ are identical or different and are 1,4-phenylene, in which one or two H atoms may be replaced by F or CN, pyridine-2,5-diyl, in which one or two H atoms may be replaced by F, pyrimidine-2,5-diyl, in which one or two H atoms may be replaced by F, trans-1,4-cyclohexylene, 1,3,4-thiadiazole-2,5-diyl or naphthalene- 2,6-diyl;
   $M^1$, $M^2$ and $M^3$ are identical or different and are —CO—O—, —O—CO—, —$CH_2$—O—, —O—$CH_a$— or —$CH_2$—$CH_2$—, and
   a, b, c, d, e and f are zero or one, with the proviso that the sum a+c+e is 0, 1, 2 or 3.

2. A liquid-crystal mixture as claimed in claim 1, which comprises from 0.1 to 80% by weight of one or more compounds of the formula I.

3. A liquid-crystal mixture as claimed in claim 1, which comprises from 0.1 to 80% by weight of one or more compounds of the formula II.

4. A liquid-crystal mixture as claimed in claim 1, which comprises from 2 to 20 components.

5. A liquid-crystal mixture as claimed in claim 1, which is ferroelectric.

6. A liquid-crystal mixture as claimed in claim 1, wherein the radicals $R^1$ and $R^2$ in the formula I are identical or different and are a straight-chain alkyl group having 6 to 12 carbon atoms.

7. A liquid-crystal mixture as claimed in claim 1, wherein, in the formula II, the symbols and indices have the following meanings:
   $R^1$ is a straight-chain alkyl radical having 1 to 14 carbon atoms, where one or two non-adjacent —$CH_2$— groups may also be replaced by —O—, —CO—, —CO—O—, —O—CO—, —O—CO—O— or —Si($CH_3$)$_2$—; and
   $A^1$, $A^2$, $A^3$ and $A^4$ are identical or different and are 1,4-phenylene, pyrimidine-2,5-diyl, in which one or two H atoms may also be replaced by F, trans- 1,4-cyclohexylene, 1,3,4-thiadiazole-2,5-diyl, pyridine-2,5-diyl, in which one or two H atoms may also be replaced by F.

8. An electro-optical switching and display element comprising a liquid-crystal mixture as claimed in claim 1.

9. A liquid-crystal mixture as claimed in claim 1, comprising 4-(5-heptanoyloxypyrimidin-2-yl)phenyl nonanoate.

10. A liquid-crystal mixture as claimed in claim 1, further comprising at least one additional chiral, non-racemic compound.

11. A liquid-crystal mixture as claimed in claim 1, comprising one to five compounds of the formula I and one to five compounds of the formula II.

12. A liquid-crystal mixture as claimed in claim 1, comprising one to three compounds of the formula I and one to three compounds of the formula II.

13. A liquid-crystal mixture as claimed in claim 1, further comprising at least one phenylpyrimidine derivative.

14. A liquid-crystal mixture as claimed in claim 1, further comprising at least one meta-substituted aromatic compound having a six-membered ring.

15. A liquid-crystal mixture as claimed in claim 1, further comprising at least one silicon compound.

16. A liquid-crystal mixture as claimed in claim 1, further comprising at least one hydroquinone derivative.

17. A liquid-crystal mixture as claimed in claim 1, further comprising at least one pyridylpyrimidine.

18. A liquid-crystal mixture as claimed in claim 1, further comprising at least one phenylbenzoate.

19. A liquid-crystal mixture as claimed in claim 1, further comprising at least one macrocyclic compound.

20. An electro-optical switching and display element as claimed in claim 8, further comprising at least one alignment layer, at least one electrode and a limiting plate.

* * * * *